(12) United States Patent
Hecht et al.

(10) Patent No.: US 8,236,871 B2
(45) Date of Patent: Aug. 7, 2012

(54) POLYMERIZABLE COMPOSITIONS CONTAINING SALTS OF BARBITURIC ACID DERIVATIVES

(75) Inventors: Reinhold Hecht, Kaufering (DE); Manfred Ludsteck, Geretsried (DE); Gioacchino Raia, Tüerkenfeld (DE); Joel D. Oxman, Minneapolis, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 12/302,591

(22) PCT Filed: May 31, 2007

(86) PCT No.: PCT/US2007/070031
§ 371 (c)(1),
(2), (4) Date: Nov. 26, 2008

(87) PCT Pub. No.: WO2007/140440
PCT Pub. Date: Dec. 6, 2007

(65) Prior Publication Data
US 2009/0192239 A1    Jul. 30, 2009

(30) Foreign Application Priority Data
May 31, 2006 (EP) ................................ 06011176

(51) Int. Cl.
*A61K 6/00* (2006.01)
*C08J 3/28* (2006.01)
*C08F 2/50* (2006.01)

(52) U.S. Cl. ............. 522/24; 522/26; 522/182; 522/83; 523/115; 523/116; 523/117; 523/118

(58) Field of Classification Search .......... 523/113–120; 522/26, 50, 171, 182, 183, 24, 83
See application file for complete search history.

(56) References Cited

U.S. PATENT DOCUMENTS

| | | |
|---|---|---|
| 4,259,075 A | 3/1981 | Yamauchi |
| 4,298,738 A | 11/1981 | Lechtken |
| 4,324,744 A | 4/1982 | Lechtken |
| 4,356,296 A | 10/1982 | Griffith |
| 4,385,109 A | 5/1983 | Lechtken |
| 4,499,251 A | 2/1985 | Omura |
| 4,503,169 A | 3/1985 | Randklev |
| 4,537,940 A | 8/1985 | Omura |
| 4,539,382 A | 9/1985 | Omura |
| 4,642,126 A | 2/1987 | Zador |
| 4,648,843 A | 3/1987 | Mitra |
| 4,652,274 A | 3/1987 | Boettcher |
| 4,665,217 A | 5/1987 | Reiners |
| 4,695,251 A | 9/1987 | Randklev |
| 4,710,523 A | 12/1987 | Lechtken |
| 4,737,593 A | 4/1988 | Ellrich |
| 4,752,338 A | 6/1988 | Reiners |
| 4,872,936 A | 10/1989 | Engelbrecht |
| 4,873,269 A * | 10/1989 | Nakazato ...................... 523/115 |
| 5,026,902 A | 6/1991 | Fock |
| 5,076,844 A | 12/1991 | Fock |
| 5,130,347 A | 7/1992 | Mitra |
| 5,154,762 A | 10/1992 | Mitra |
| 5,166,117 A * | 11/1992 | Imai et al. ...................... 502/169 |
| 5,290,172 A * | 3/1994 | Sakuma et al. ............... 433/215 |
| 5,501,727 A | 3/1996 | Wang |
| 5,530,038 A | 6/1996 | Yamamoto |
| 5,545,676 A | 8/1996 | Palazzotto |
| 6,251,963 B1 | 6/2001 | Kohler |
| 6,288,138 B1 * | 9/2001 | Yamamoto et al. ........... 523/118 |
| 6,387,979 B1 | 5/2002 | Hino |
| 6,387,981 B1 | 5/2002 | Zhang |
| 6,458,868 B1 | 10/2002 | Okada |
| 6,566,413 B1 | 5/2003 | Weinmann |
| 6,572,693 B1 | 6/2003 | Wu |
| 6,624,236 B1 | 9/2003 | Bissinger |
| 6,730,156 B1 | 5/2004 | Windisch |
| 6,852,775 B1 * | 2/2005 | Soglowek et al. ............ 523/109 |
| 6,852,795 B2 | 2/2005 | Bissinger |
| 6,852,822 B1 | 2/2005 | Bissigner |
| 6,899,948 B2 | 5/2005 | Zhang |
| 6,953,535 B2 * | 10/2005 | Hecht et al. ............... 252/183.13 |
| 7,037,962 B2 | 5/2006 | Destro |
| 7,090,721 B2 | 8/2006 | Craig |
| 7,090,722 B2 | 8/2006 | Budd |
| 7,156,911 B2 | 1/2007 | Kangas |
| 7,214,726 B2 * | 5/2007 | Qian ............................ 523/116 |
| 7,393,882 B2 | 7/2008 | Wu |
| 7,488,762 B2 * | 2/2009 | Takano et al. .................. 523/117 |
| 7,649,029 B2 | 1/2010 | Kolb |
| 7,879,924 B2 * | 2/2011 | Torii et al. ...................... 523/116 |
| 7,989,519 B2 * | 8/2011 | Vogt et al. ...................... 523/115 |

(Continued)

FOREIGN PATENT DOCUMENTS
DE        19 757 277        6/1999
(Continued)

OTHER PUBLICATIONS

Brederick, "Uber CH-aktive Polymerisationsinitiatoren", *Makromol Chem.* vol. 92, pp. 70-90, (1966).
Imai, "Importance of Polymerization Initiator Systems and Interfacial Initiation of Polymerization in Adhesive Bonding of Resin to Dentin", *Journal of Dental Research*, vol. 70, No. 7, pp. 1088-1091, (1991).
Webster, Chemistry & Technology of UV & EB Formulation for coatings, Inks & Paints, *Prepolymers & Reactive Diluents*, vol. II, Chapter II pp. 35-256, (1997).
Search Report European Application No.—Extended—EP10170840, 4 pgs, Jan. 17, 2007.

(Continued)

*Primary Examiner* — Susan W Berman
(74) *Attorney, Agent, or Firm* — Pamela L. Stewart

(57) ABSTRACT

This invention relates to polymerizable compositions comprising a salt of a barbituric acid derivative. The compositions are typically shelf-life stable and may be polymerized through mixing of an acidic component with the salt of a barbituric acid derivative.

21 Claims, No Drawings

U.S. PATENT DOCUMENTS

| | | | |
|---|---|---|---|
| 2003/0094225 A1 | 5/2003 | Knowlton | |
| 2003/0195273 A1 | 10/2003 | Mitra | |
| 2003/0215635 A1 | 11/2003 | Johnson | |
| 2004/0110864 A1* | 6/2004 | Hecht et al. | 523/113 |
| 2004/0206932 A1 | 10/2004 | Abuelyaman | |
| 2005/0014861 A1* | 1/2005 | Qian | 523/116 |
| 2010/0016466 A1* | 1/2010 | Lueck | 523/116 |

FOREIGN PATENT DOCUMENTS

| | | |
|---|---|---|
| EP | 0 173 567 | 3/1986 |
| EP | 0 201 031 | 11/1986 |
| EP | 0 201 778 | 11/1986 |
| EP | 0 373 384 | 6/1990 |
| EP | 0 480 785 | 9/1991 |
| EP | 0 712 622 | 5/1996 |
| EP | 0 923 924 | 6/1999 |
| EP | 1 051 961 | 11/2000 |
| EP | 1 413 599 | 4/2004 |
| EP | 1 502 569 | 2/2005 |
| JP | 63035508 | 2/1988 |
| JP | 4126703 | 4/1992 |
| JP | 05345806 | 12/1993 |
| JP | 2006-299202 | 11/2006 |
| WO | WO 00/38619 | 7/2000 |
| WO | WO 00/42092 | 7/2000 |
| WO | WO 01/07444 | 2/2001 |
| WO | WO 01/30305 | 5/2001 |
| WO | WO 01/30306 | 5/2001 |
| WO | WO 01/30307 | 5/2001 |
| WO | WO 01/92271 | 12/2001 |
| WO | WO 02/092023 | 11/2002 |
| WO | WO 03/063804 | 8/2003 |

OTHER PUBLICATIONS

Search Report European Application No. EP06011176, 4 pgs, Nov. 15, 2006.

Search Report of International Application No. PCT/US2007/070031, 4 pgs, Jan. 8, 2008.

Written Opinion of International Application No. PCT/US2007/070031, 5 pgs, Jan. 8, 2008.

* cited by examiner

POLYMERIZABLE COMPOSITIONS CONTAINING SALTS OF BARBITURIC ACID DERIVATIVES

CROSS REFERENCE TO RELATED APPLICATIONS

This application is a national stage filing under 35 U.S.C. 371 of PCT/US2007/070031, filed May 31, 2007, which claims priority to European Patent Application No. 06011176.2, filed May 31, 2006, the disclosure of which is incorporated by reference in its entirety herein.

FIELD OF THE INVENTION

This invention relates to polymerizable compositions. More specifically, the invention relates to polymerizable compositions containing salts of barbituric acid derivatives.

BACKGROUND

Barbituric and thiobarbituric acid and their derivatives have been used as components of redox initiating systems in polymerizable compositions. In particular, barbituric acid in combination with a halogen compound and a metal ion has been found to be efficient in curing methacrylates. For example, a polymer initiating system containing a barbituric or thiobarbituric acid compound and a copper or ferrum halogenide has been used for curing methacrylate compositions. An initiating system using a barbituric acid derivative and copper (II) chloride has also been used. An initiating system comprising barbituric or thiobarbituric acid derivative, a copper salt, and a sulfinic acid compound has been used for curing unsaturated, acidic resins. However, conventional initiating systems that use barbituric acid, thiobarbituric acid, and/or their derivatives as part of redox initiating system generally do not provide shelf-life stable compositions in contact with unsaturated compounds, such as, e.g., methacrylates. Thus, there is a need to have an improved polymerizable composition with enhanced shelf-life stability.

SUMMARY

The present invention is directed to polymerizable compositions comprising at least one salt of a barbituric acid derivative. In addition, the polymerizable compositions also typically include a non-acidic polymerizable component. The mixing of the salt with a non-acidic, free-radically polymerizable component can yield a polymerizable composition having a stable formulation with sufficient shelf-life to be useful in commercial applications. Such a formulation may, in turn, be mixed with an acidic composition to initiate polymerization.

As used herein the term "barbituric acid derivative" includes barbituric acid, barbituric acid derivatives, thiobarbituric acid, and thiobarbituric acid derivatives. The salt may comprise a metal cation or inorganic cation. Suitable metal cations include any metals M that are able to provide stable cations $M^+$, $M^{2+}$, or $M^{3+}$. Some possible inorganic cations include the cations of Li, Na, K, Mg, Ca, Sr, Ba, Al, Fe, Cu, Zn, or La. An exemplary salt of barbituric acid is the calcium salt of 1-benzyl-5-phenyl-barbituric acid. Another example of a suitable barbituric acid salt is the sodium salt of 1-benzyl-5-phenyl-barbituric acid. One possible salt of a thiobarbituric acid derivative is the calcium salt of 5-phenyl-thiobarbituric acid.

In some implementations, the salt may comprise an organic cation. Suitable possible organic cations include the cations of amines, such as a cation of ammonium or a cation of alkylammonium. One example of this type of barbituric acid salt is the triethanolammonium salt of 1-benzyl-5-phenyl-barbituric acid.

The non-acidic free radically polymerizable component may comprise an acrylate or methacrylate. In some embodiments, the methacrylate may be triethyleneglycol dimethacrylate, propoxylated Bisphenol A dimethacrylate, or a mixture of the two.

Compositions of the invention further include polymerizable compositions that comprise a combination of salt of a barbituric acid derivative, a non-acidic polymerizable component, and an acidic component or a precursor to an acidic component. The acidic component or precursor to an acidic component may be polymerizable, and may be an ethylenically unsaturated compound, such as, for example, 1,3 glycerol dimethacrylate phosphate.

Typically, the mixing of the salt of a barbituric acid derivative and non-acidic polymerizable component together with the acidic component or precursor to an acidic component causes the resulting mixture to polymerize. In some embodiments, the acidic component or precursor to an acidic component has a pKa lower than that of the barbituric acid derivative.

In one embodiment, the hardenable composition comprises the calcium salt of 1-benzyl-5-phenyl barbituric acid, triethyleneglycol dimethacrylate, propoxylated Bisphenol A dimethacrylate, and 1,3 glycerol dimethacrylate phosphate. In other embodiments, the calcium salt of 1-benzyl-5-phenyl barbituric acid is replaced by the sodium salt of 1-benzyl-5-phenyl-barbituric acid, calcium salt of 5-phenyl-thiobarbituric acid, or the triethanolammonium salt of 1-benzyl-5-phenyl-barbituric acid. The polymerizable composition may further comprise one or more additives selected from the group consisting of a water adsorbent, a fumed silica, a stabilizer, an accelerator, a pigment, a photoinitiator system, or a stabilizer. The polymerizable composition may also comprise one or more fillers.

The invention also includes kits. One potential feature of the kit is that it may contain two or more pastes that are mixed to initiate polymerization. The mixing of two or more pastes may offer increased miscibility as opposed to previously used powder and liquid systems. A kit according to the invention may include one or more pastes containing together or in separate parts: a salt of a barbituric acid derivative, a non-acidic polymerizable component, and/or an acidic polymerizable component. The kits also typically include a means for mixing the pastes.

The invention also includes redox initiator systems comprising a salt of a barbituric acid derivative, an acidic compound or precursor to an acidic compound, and a copper compound. The redox initiator system may further comprise a visible light sensitizer.

In another aspect, the invention is directed to a method for curing a polymerizable composition. This method comprises preparing a first composition comprising a salt of a barbituric acid derivative and a non-acidic polymerizable component, preparing a second composition comprising an acidic component or precursor to an acidic component, and mixing the first and second compositions together. In some embodiments, the acidic component or precursor to an acidic composition may be polymerizable.

Certain embodiments of the invention will contain one or more additives such as a water adsorbent component, a photoinitiator, a stabilizer, a fumed silica, an accelerator, or a pigment. Other additives may also be present in certain embodiments. Certain embodiments may also contain one or more fillers.

The invention may provide one or more advantages. For example, polymerizable compositions cured by initiator systems containing barbituric acid derivatives typically exhibit good color stability and mechanical properties. In addition, the curing of these formulations may produce less heat in comparison to other redox initiating systems. One possible advantage realized by the mixture of a salt of a barbituric acid derivative with a non-acidic polymerizable compound is the stability of said mixture allowing it to be stored for a long period of time. Previous formulations were unable to store barbituric acid derivatives with monomer because the mixture prematurely polymerized.

Another potential advantage of the invention is the improved miscibility realized due to the stable mixture of the salt of a barbituric acid derivative with a polymerizable component in a paste. Previous formulations separated the barbituric acid component and the polymerizable component because of the reactivity and introduced the barbituric acid as a powder. Improved miscibility may be achieved upon mixing of two pastes rather than a powder and liquid. Improved miscibility is desirable when the invention is used in a dental environment in order to provide easier handling for dentists.

Other features, objects, and advantages of the invention will be apparent from the following detailed description and from the claims.

DEFINITIONS

The recitation of numerical ranges by endpoints includes all numbers subsumed within that range (e.g. 1 to 5 includes 1, 1.5, 2, 2.75, 3, 3.80, 4, and 5). The terms "include", "contain", or "comprise" introduce a nonexclusive enumeration of features.

As used in this specification and the appended claims, the singular forms "a", "an", and "the" include plural referents unless the content clearly dictates otherwise. Thus, for example, reference to a composition containing "a compound" includes a mixture of two or more compounds. Similarly, the terms "a", "an", "the" and "one" are to be understood in the sense of "at least one".

As used in this specification and the appended claims, the term "or" is generally employed in its sense including "and/or" unless the content clearly dictates otherwise.

The term "non-acidic polymerizable" composition includes ethylenically unsaturated compounds without acid functionality.

DETAILED DESCRIPTION

The invention provides compositions that may be used for treating hard surfaces such as dentin, enamel, and bone. The compositions can be used with an adhesive (e.g., a dental adhesive) as a luting cement, a filling material, a core build-up material or a pit and fissure sealant. The compositions can also be formulated to be self-adhesive and can be used e.g. as a luting cement, a filling material or a core build-up material without any additional adhesive.

Compositions of the invention can optionally contain fillers, water adsorbents, fumed silicas, visible light sensitizers, stabilizers, and other additives. Various combinations of the components described herein can be used in the compositions of the invention.

Compositions of the invention can also contain a polymerizable component. One polymerizable composition comprises the following constituents: (A) a salt of a barbituric acid derivative, and (B) an ethylenically unsaturated compound without acid functionality.

Compositions of the invention include a salt of a barbituric acid derivative having of the general structure:

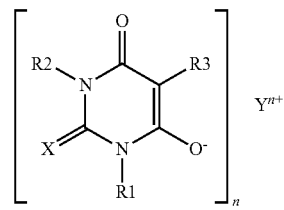

In this structure R1, R2, and R3, which may be identical or different, are independently selected from the following: hydrogen, alkyl, substituted alkyl, alkenyl, cycloalkyl, substituted cycloalkyl, arylalkyl, aryl or substituted aryl radical. R1, R2, and R3 may also incorporate a halogen radical such as chloro or a hydroxyl, amino or nitro group.

If one of the radicals R1 to R3 is unsubstituted alkyl then this radical can be straight-chain or branched and can contain, for example, from 1 to 18 carbon atoms, preferably from 1 to 10, and in particular from 1 to 6 carbon atoms. Examples of low-molecular alkyl radicals include methyl, ethyl, propyl, isopropyl, n-butyl, t-butyl, isobutyl, n-pentyl, and isoamyl.

If one of the radicals R1 to R3 is a substituted alkyl radical then the alkyl moiety of this radical typically has the number of carbon atoms indicated above for unsubstituted alkyl. If one of the radicals R1 to R3 is alkoxyalkyl or alkoxycarbonylalkyl then the alkoxy radical typically contains, for example, from 1 to 5 carbon atoms and is most typically methyl, ethyl, propyl, isopropyl, n-butyl, t-butyl, isobutyl, n-pentyl or isoamyl. If one of the radicals R1 to R3 is haloalkyl then the halo moiety is understood to be fluoro, chloro, bromo or iodo.

If one of the radicals R1 to R3 is alkenyl, it is typically a C3 to C5 alkenyl radical, especially allyl.

If one of the radicals R1 to R3 is unsubstituted cycloalkyl, it is typically a C4 to C7 cyclo-alkyl radical, such as cyclopentyl or cyclohexyl. If one of the radicals R1 to R3 is a substituted cycloalkyl then it is typically one of the above-indicated cycloalkyl radicals, with the substituent or substituents on the cycloalkyl radical possibly being, for example, C1 to C4 alkyl such as methyl, ethyl, propyl, n-butyl or isobutyl, fluoro, chloro, bromo, iodo or C1 to C4 alkoxy, especially methoxy. If one of the radicals R1 to R3 is aryl or aralkyl, then it is typically a phenyl or naphthyl as aryl. Particularly suitable arylalkyl radicals are benzyl and phenylethyl.

R1 to R3 may also be substituted aryl radicals if desired. In this case phenyl and naphthyl are preferred and as ring substituents C1 to C4 alkyl, especially methyl, halogen or $C_1$ to $C_4$ alkoxy, especially methoxy.

X is oxygen or sulfur.

Y may be an organic cation or an inorganic cation. The inorganic cation can be, but is not limited to, any metal M that is able to provide a cation M+, M2+, or M3+. Suitable inorganic cations include the cations of Li, Na, K, Mg, Ca, Sr, Ba, Al, Fe, Cu, Zn, or La.

The organic cation may be a cation derived from ammonia or primary, secondary or tertiary amines. The substituents of primary, secondary or tertiary amines include alkyl, substituted alkyl, alkenyl, cycloalkyl, substituted cycloalkyl, arylalkyl, aryl or substituted aryl or mixtures thereof.

Examples of suitable primary amines include methylamine, ethylamine, propylamine, isopropylamine, n-butylamine, isobutylamine, tert.-butylamine, pentylamine, hexylamine, octylamine, ethanolamine, monoallylamine, cyclopentylamine, cyclohexylamine, benzylamine, phenylethylamine, phenylamine, naphthylamine.

Examples of suitable secondary amines include dimethylamine, diethylamine, ethylmethylamine, dipropylamine, diisopropylamine, di-n-butylamine, diisobutylamine, di-tert.-butylamine, dipentylamine, dihexylamine, dioctylamine, diethanolamine, diallylamine, dicyclopentylamine, dicyclohexylamine, dibenzylamine, diphenylethylamine, diphenylamine, dinaphthylamine.

Examples of suitable tertiary amines include trimethylamine, triethylamine, tripropylamine, triisopropylamine, tri-n-butylamine, triisobutylamine, tri-tert.-butylamine, tripentylamine, trihexylamine, trioctylamine, triethanolamine, Dimethylethanolamine, N,N-dimethylaminoethylmethacrylate, triallylamine, tricyclopentylamine, tricyclohexylamine, tribenzylamine, triphenylethylamine, triphenylamine, trinaphthylamine.

Besides the above listed examples of primary, secondary or tertiary amines containing one nitrogen atom per molecule, also aminic compounds having two or more nitrogen atoms per molecule (so called polyamines) can be used according to the invention to prepare organic salts of barbituric or thiobarbituric acid derivatives. Examples of suitable polyamines include ethylenediamine, diethylenetriamine, triethylenetetramine, 1,6-hexa-methylenediamine, hydrazine, 1,3- and 1,4-phenylenediamine, 1-amino-3-aminomethyl-3,5,5-trimethylcyclohexan (=isophoronediamine), 4,4'-diphenylmethandiamine, amino-functional polyethylene oxide resp. polypropylene oxide (known as Jeffamin, D-series).

The preparation of a salt of a barbituric acid derivative is known in the art and is illustrated in the examples.

The following are exemplary representatives of barbituric acid derivatives which may be used to make constituent (A): barbituric acid, thiobarbituric acid, 1,3,5-trimethylbarbituric acid, 1-phenyl-5-benzylbarbituric acid, 1-benzyl-5-phenylbarbituric acid, 1,3-dimethylbarbituric acid, 1,3-dimethyl-5-phenylbarbituric acid, 1-cyclohexyl-5-ethylbarbituric acid, 5-laurylbarbituric acid, 5-butylbarbituric acid, 5-allylbarbituric acid, 5-phenylthiobarbituric acid, 1,3-dimethylthiobarbituric acid, trichlorobarbituric acid, 5-nitrobarbituric acid, 5-aminobarbituric acid, and 5-hydroxybarbituric acid.

Compositions of the invention include ethylenically unsaturated compounds without acid functionality. These compounds are polymerizable and may be monomers, oligomers, or polymers.

Typically, the compositions of the invention are chemically polymerizable. These compositions include a polymerizable component (e.g., an ethylenically unsaturated polymerizable component) and the inorganic or organic salt of a barbituric acid derivative, which may act as a polymerization initiator.

In one embodiment, the ethylenically unsaturated component includes α,β-unsaturated compounds, which can provide altered properties such as toughness, adhesion, set time, and the like. When α,β-unsaturated compounds are employed, they preferably are water-insoluble or water-miscible, but can also be water-soluble or water-dispersible. Water-insoluble, water-soluble, water-miscible, or water-dispersible (meth)acrylates (i.e., acrylates and methacrylates), (meth)acrylamides (i.e., acrylamides and methacrylamides), and urethane (meth)acrylates are preferred.

Examples include, but are not limited to mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)-acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]-propane (bisGMA).

Suitable ethylenically unsaturated compounds are also available from a wide variety of commercial sources, such as Sigma-Aldrich, St. Louis, Mo. and Rohm and Tech, Inc., Darmstadt, Germany. Further suitable mono- and polyfunctional acrylates and methacrylates and further ethylenically unsaturated compounds are also described in G. Webster (Ed.), Chemistry & Technology of UV & EB Formulation for Coatings, Inks and Paints, Vol. II Prepolymers and Reactive Diluents, J. Wiley and Sons, Chichester, N.Y., Weinheim, Brisbane, Toronto, Singapore, 1997. Mixtures of α,β-unsaturated compounds can be used if desired.

Other examples of useful ethylenically unsaturated compounds include acrylic acid esters, methacrylic acid esters, hydroxy-functional acrylic acid esters, hydroxy-functional methacrylic acid esters, and combinations thereof.

Typically, the compositions of the invention include a sufficient quantity of ethylenically unsaturated component to provide the desired setting or hardening rate and desired overall properties following hardening.

The polymerizable composition may also include an ethylenically unsaturated compound with acid functionality. Accordingly, in one embodiment of the invention, the polymerizable composition comprises the following constituents:

(A) a salt of a barbituric acid derivative, (B) an ethylenically unsaturated compound without acid functionality, and (C) an ethylenically unsaturated compound with acid functionality.

An ethylenically unsaturated compound with acid functionality can be used to initiate polymerization of the formulation by activating the inorganic or organic salt of the barbituric acid derivative. This activation may take place by mixing a paste or liquid mixture which comprises an inorganic or organic salt of a barbituric acid derivative and an ethylenically unsaturated compound without acid functionality with a paste or liquid mixture comprising an ethylenically unsaturated compound with acid functionality. Upon mixing and contacting with the inorganic or organic salt, the ethylenically unsaturated compound with acid functionality activates the inorganic or organic salt of the barbituric acid derivative. The activation of the inorganic or organic salt of the barbituric acid derivative initiates polymerization of the ethylenically unsaturated compounds.

As used herein, "ethylenically unsaturated compounds with acid functionality" is meant to include monomers, oligomers, and polymers having ethylenic unsaturation and acid and/or acid-precursor functionality. Acid-precursor functionalities include, for example, anhydrides, acid halides, and pyrophosphates.

Suitable ethylenically unsaturated compounds with acid functionality include, for example, hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, α,β-unsaturated acidic compounds such as glycerol phosphate monomethacrylates, glycerol phosphate dimethacrylates, caprolactone methacrylate phosphate, citric acid di- or trimethacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonic acid, poly(meth)acrylated polyboric acid, and combinations thereof. Also monomers, oligomers, and polymers of unsaturated carbonic acids such as (meth)acrylic acids, aromatic (meth)acrylated acids (e.g., methacrylated trimellitic acids), and anhydrides thereof can be used. In some implementations, the compositions of the invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. Nos. 4,872,936 (Engelbrecht) and 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Patent Application Publication No. 2004/0206932 (Abuelyaman); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. Nos. 4,259,075 (Yamauchi et al.), 4,499,251 (Omura et al.), 4,537,940 (Omura et al.), 4,539,382 (Omura et al.), 5,530,038 (Yamamoto et al.), 6,458,868 (Okada et al.), and European Pat. Application Publication Nos. EP 712,622 (Tokuyama Corp.) and EP 1,051,961 (Kuraray Co., Ltd.).

In other implementations, the compositions may contain an acid or precursor to an acid without an ethylenically unsaturated functionality. Examples of suitable acid groups are carboxylic acid residues, acid residues of phosphorous (e.g. phosphoric, phosphonic, phosphinic acids), of sulfur (e.g. sulfuric, sulfonic, sulfinic acids) and of boron. The acid residues can be available in free form, but also in derivatized form such as for example anhydrides, acid halides or pyrophosphates. Suitable acids or acid precursors include acetic acid, acetic acide anhydride, acetic acid chloride, propionic acid, citric acid, benzoic acid, benzoic acid chloride, polycarboxylic acid, phosphoric acid, polyphosphonic acid, sulfuric acid, benzene sulfinic acid, toluene sulfinic acid, benzene sulfonic acid, toluene sulfonic acid and polysulfonic acid.

The chemically polymerizable compositions may include additional redox cure systems. The reducing and oxidizing agents typically react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. Typically, the reducing and oxidizing agents are sufficiently shelf-stable and free of undesirable colorization to permit their storage and use under typical dental conditions, and are sufficiently miscible with the resin system to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate.

This can be evaluated by combining all of the ingredients of the polymerizable composition except for the optional filler, and observing whether or not a hardened mass is obtained.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a photo-polymerizable composition such as described U.S. Pat. No. 5,154,762 (Mitra et al.).

In certain embodiments, the compositions are photopolymerizable, i.e., the compositions contain a photoinitiator (i.e., a photoinitiator system) that upon irradiation with actinic radiation initiates the polymerization (or hardening) of the free radically polymerizable composition.

Photopolymerizable compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxy-phenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth) acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)-acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]-propane (bisGMA). Suitable ethylenically unsaturated compounds are also available from a wide variety of commercial sources, such as Sigma-Aldrich, St. Louis. Further suitable mono- and polyfunctional acrylates and methacrylates and further ethylenically unsaturated compounds are also described in G. Webster (Ed.), Chemistry & Technology of UV & EB Formulation for Coatings, Inks and Paints, Vol. II Prepolymers and Reactive Diluents, J. Wiley and Sons, Chichester, N.Y., Weinheim, Brisbane, Toronto, Singapore, 1997. Mixtures of ethylenically unsaturated compounds can be used if desired).

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Suitable iodonium salts include the diaryl iodonium salts, e.g., diphenyliodonium chloride, diphenyliodonium hexafluorophosphate, diphenyl-iodonium tetrafluoroborate, and tolylcumyliodonium tetrakis(pentafluorophenyl)borate. Suitable photosensitizers are monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphorquinone, benzil, furil, 3,3,6,6-tetramethylcyclo-hexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate.

Other suitable photoinitiators for polymerizing free radically photopolymerizable compositions include the class of phosphine oxides that typically have a functional wavelength range of about 380 nm to about 1200 nm. Examples of phosphine oxide free radical initiators with a functional wavelength range of about 380 nm to about 450 nm include acyl and bisacyl phosphine oxides such as those described in U.S. Pat. Nos. 4,298,738 (Lechtken et al.), 4,324,744 (Lechtken et al.), 4,385,109 (Lechtken et al.), 4,710,523 (Lechtken et al.), and 4,737,593 (Ellrich et al.), 6,251,963 (Kohler et al.); and EP Application No. 0 173 567 A2 (Ying).

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino)benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

The polymerizable composition may also include one or more fillers. The filler is often finely divided. The filler can have a unimodial or polymodial (e.g., bimodal) particle size distribution. Typically, the maximum particle size (the largest dimension of a particle, typically, the diameter) of the filler is less than about 20 micrometers, more typically less than about 10 micrometers, and most typically less than about 5 micrometers. Typically, the average particle size of the filler is less than about 0.1 micrometers, and more typically less than about 0.075 micrometer.

The filler can be an inorganic material. It can also be a crosslinked organic material that is insoluble in the resin system (i.e., the hardenable components), and is optionally filled with inorganic filler. When used in a dental application, the filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz (i.e., silica, $SiO_2$); nitrides (e.g., silicon nitride); glasses and fillers derived from, for example, Zr, Sr, Ce, Sb, Sn, Ba, Zn, and Al; feldspar; borosilicate glass; kaolin; talc; zirconia; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polymethacrylates polyepoxides, and the like.

Suitable non-acid-reactive filler particles are quartz (i.e., silica), submicron silica, zirconia, submicron zirconia, and non-vitreous microparticles of the type described in U.S. Pat. No. 4,503,169 (Randklev). Mixtures of these non-acid-reactive fillers are also contemplated, as well as combination fillers made from organic and inorganic materials.

The filler can also be an acid-reactive filler. Suitable acid-reactive fillers include metal oxides and hydroxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other components and will perform well if the resulting mixture is used in the mouth.

Generally, the average particle size (typically, diameter) for the FAS glass is no greater than 12 micrometers, typically no greater than about 10 micrometers, and more typically no greater than about 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxy-silane, gamma-aminopropyltrimethoxysilane, and the like. Silane-treated zirconia-silica ($ZrO_2$-$SiO_2$) filler, silane-treated silica filler, silane-treated zirconia filler, and combinations thereof are especially preferred in certain embodiments.

Other suitable fillers are disclosed in U.S. Pat. Nos. 6,387,981 (Zhang et al.) and 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. patent application Ser. Nos. 10/847,781 (Kangas et al.); 10/847,782 (Kolb et al.); 10/847,803 (Craig et al.); and 10/847,805 (Budd et al.) all four of which were filed on May 17, 2004.

For some embodiments (e.g. where the composition is a dental adhesive) the compositions preferably include at least about 1% by weight, more preferably at least about 2% by weight, and most preferably at least about 5% by weight filler, based on the total weight of the composition. For such embodiments, compositions of the invention preferably include at most about 40% by weight, more preferably at most about 20% by weight, and most preferably at most about 15% by weight filler, based on the total weight of the composition.

For other embodiments (e.g., where the composition is a dental restorative or an orthodontic adhesive), compositions of the present invention preferably include at least about 40% by weight, more preferably at least about 45% by weight, and most preferably at least about 50% by weight filler, based on the total weight of the composition. For such embodiments, compositions of the invention preferably include at most about 90% by weight, more preferably at most about 80% by weight, even more preferably at most about 70% by weight filler, and most preferably at most about 50% by weight filler, based on the total weight of the composition.

Optionally, compositions of the invention may contain solvents (e.g., water, alcohols (e.g., propanol, ethanol), ketones (e.g., acetone, methyl ethyl ketone), esters (e.g., ethyl acetate), and other nonaqueous solvents (e.g., dimethylformamide, dimethylacetamide, dimethylsulfoxide, 1-methyl-2-pyrrolidinone)).

If desired, the compositions of the invention can contain additives. Suitable additives and their functions are described e.g. in P. Nanetti, Lackrohstoffkunde, Vincentz Verlag, Hanover 1997. Examples of additives include indicators, dyes, pigments, inhibitors, accelerators, viscosity modifiers, wetting agents, emulsifying agents, tartaric acid, chelating agents, buffering agents, stabilizers, and other similar ingredients that will be apparent to those skilled in the art. Additionally, medicaments or other therapeutic substances can be optionally added to the compositions. Examples include, but are not limited to, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Certain compositions of the invention may contain an adsorbent component. An adsorbent component may contain synthetic zeolites. Some adsorbents components only absorb water, while others can absorb other molecules as well.

The salts of the barbituric acid derivatives of the invention can be used as a part of a redox initiator system. The redox initiator system may comprise the following constituents: (A) an inorganic or organic salt of a barbituric acid derivative, (B) an acidic compound, and (C) a copper compound. The redox initiator system of the invention can be used for preparing and applying adhesion-promoting substances, dental fixing compositions and dental filling materials with variable filler content. The redox initiator system of the invention is also suitable for curing coating materials and/or adhesives based on ethylenically unsaturated monomers.

The redox initiator system of the invention is suitable for curing acidic formulations based on ethylenically unsaturated monomers, (meth)acrylates for example.

A specific embodiment of the redox intiator system comprises as component (B) a sulfinic acid compound and/or mixtures thereof of the general formula R1SOO—R2, in which R1 is an alkyl, substituted alkyl, alkenyl, cycloalkyl, substituted cycloalkyl, arylalkyl, aryl or substituted aryl radical and R2=H, metal such as lithium, sodium or potassium or is an alkyl, substituted alkyl, alkenyl, cycloalkyl, substituted cycloalkyl, arylalkyl, aryl or substituted aryl radical.

If one of the radicals R1 or R2 is unsubstituted alkyl then this radical can be straight-chain or branched and can contain, for example, from 1 to 18 carbon atoms, preferably from 1 to 10, and in particular from 1 to 6 carbon atoms. Examples of low-molecular alkyl radicals are methyl, ethyl, propyl, isopropyl, n-butyl, t-butyl, isobutyl, n-pentyl, and isoamyl.

If one of the radicals R1 or R2 is a substituted alkyl radical then the alkyl moiety of this radical typically has the number of carbon atoms indicated above for unsubstituted alkyl. If one of the radicals R1 or R2 is alkoxyalkyl or alkoxycarbonylalkyl then the alkoxy radical contains, for example, from 1 to 5 carbon atoms and is preferably methyl, ethyl, propyl, isopropyl, n-butyl, t-butyl, isobutyl, n-pentyl or isoamyl. If one of the radicals R1 or R2 is haloalkyl then the halo moiety is understood to be fluoro, chloro, bromo or iodo.

If one of the radicals R1 or R2 is alkenyl, then it is typically a C3 to C5 alkenyl radicals, especially allyl.

If one of the radicals R1 or R2 is unsubstituted cycloalkyl, then it is typically $C_4$ to $C_7$ cycloalkyl radicals, such as cyclopentyl or cyclohexyl.

If one of the radicals R1 or R2 is substituted cycloalkyl, then it is typically one of the above-indicated cycloalkyl radicals, with the substituent or substituents on the cycloalkyl radical possibly being, for example, C1 to C4 alkyl such as methyl, ethyl, propyl, n-butyl or isobutyl, fluoro, chloro, bromo, iodo or C1 to C4 alkoxy, especially methoxy.

If one of the radicals R1 or R2 is aryl or aralkyl, then it is typically a phenyl or naphthyl as aryl. Preferred arylalkyl radicals include benzyl and phenylethyl.

R1 or R2 may also be substituted aryl radicals if desired. In this case phenyl and naphthyl are preferred and as ring substituents C1 to C4 alkyl, especially methyl, halogen or C1 to C4 alkoxy, especially methoxy.

As representatives of component (B) exemplary mention may be made of the following: benzenesulfinic acid, sodium benzenesulfinate, sodium benzenesulfinate dihydrate, sodium toluenesulfinate, formamidinesulfinic acid, sodium salt of hydroxymethanesulfinic acid, sodium salt of 2,5-dichlorobenzenesulfinic acid, 3-acetamido-4-methoxybenzenesulfinic acid.

Particularly suitable compounds of component (B) are sodium toluenesulfinate or sodium benzenesulfinate and their hydrates.

Certain compositions of the invention contain a copper compound and/or mixtures thereof possessing the general formula CuXn, where X is an organic and/or inorganic anion and n=1 or 2. Examples of suitable copper compounds include copper chloride, copper acetate, copper acetylacetonate, copper naphthenate, copper salicylate or complexes of copper with thiourea or ethylenediaminetetraacetic acid.

Certain embodiments of the invention are directed towards a kit. A kit contains components or combinations of components of the compositions that ready to be mixed together. The contents of the composition are packaged to allow for storage of the components until they are needed.

The compositions of the invention may be formulated as self-adhesive dental compositions. One self-adhesive composition comprises the following constituents: (A) a salt of a barbituric acid derivative, (B) an ethylenically unsaturated compound without acid functionality, and (C) an ethylenically unsaturated compound with acid functionality.

In another aspect, the invention provides an adhesive composition including: an ethylenically unsaturated compound with acid functionality; an ethylenically unsaturated compound without acid functionality; an initiator system comprising a salt of a barbituric acid derivative; and water, wherein the composition is a self-etching, water-in-oil emulsion (e.g., a micro-emulsion).

The polymerizable composition may be used in many settings and is not limited to any particular area. E.g., besides the dental field the inventive polymerizable composition can be used as a coating material, for adhesively fixing materials or in the construction field e.g. for fixing an anchor or a dowel in a wall.

The invention is illustrated by the following examples. It is to be understood that the particular examples, materials, amounts, and procedures are to be interpreted broadly in accordance with the scope and spirit of the invention as set forth herein. Unless otherwise indicated, all parts and percentages are on a weight basis.

EXAMPLES

Test Methods

Determination of Polymerization Time

The time required for polymerization of monomer mixtures in Examples 1-18 and Comparative Examples 1 and 2 was determined using a simple dental probe. The time required for polymerization was defined as the point where the probe could no longer be immersed in the initial liquid mixture.

Determination of Setting Time of a Paste-Paste Mixture

The setting time of the mixed paste in Example 19 was measured using a rheometer (Model MRC 301; manufactured by Anton Paar; Ostfildern, Germany) by observing the parameter tan δ, defined as the ratio of viscous modulus to elastic modulus.

Materials

A. Salts of Barbituric Acid Derivatives

1. Calcium Salt of 1-benzyl-5-phenyl-barbituric acid (Abbreviated as Ca-BzPB)

Calcium hydroxide (1.234 g) was added to 500 ml of distilled water and stirred for 10 minutes to yield a suspension having a pH of about 11. 1-benzyl-5-phenyl-barbituric acid (9.234 g) was added to the suspension with stirring resulting in an essentially clear solution having a pH of about 7. The solution was stirred for additional 30 minutes and then filtered. The filtrate was frozen with liquid nitrogen and then freeze-dried to yield the calcium salt of 1-benzyl-5-phenyl-barbituric acid as characterized by proton nuclear magnetic resonance spectroscopy ($^1$H-NMR) and infrared spectroscopy.

2. Sodium Salt of 1-benzyl-5-phenyl-barbituric acid (Abbreviated as Na-BzPB)

Na-BzPB was prepared according to the procedure above, with the exception that sodium bicarbonate was employed instead of calcium hydroxide. Specifically, 50 g of 1-benzyl-5-phenyl-barbituric acid was added to 15 g of sodium bicarbonate.

3. Triethanolammonium Salt of 1-benzyl-5-phenyl-barbituric Acid (Abbreviated as TEA-BzPB)

Triethanolamine (15.2 g) was dissolved in 600 ml of acetone and heated to 30° C. Thirty (30) g of 1-benzyl-5-phenyl-barbituric acid was added to the clear solution under stirring. After 10 minutes, the triethanol ammonium salt of 1-benzyl-5-phenyl-barbituric acid (TEA-BzPB) precipitated. After stirring for additional 16 hours, the precipitated salt was isolated by filtration, dried under vacuum (0.02 mbar) at 60° C. and then characterized by proton nuclear magnetic resonance spectroscopy ($^1$H-NMR).

4. Calcium Salt of 5-phenyl-thiobarbituric Acid (abbreviated as Ca-PTB)

Calcium hydroxide (0.331 g) was added to 50 ml of distilled water and stirred for 10 minutes to yield a suspension having a pH of about 11. 5-Phenyl-thiobarbituric acid (1.914 g) was added to the suspension. The reaction mixture was stirred for 1 hour and then filtered. The filtrate was frozen with liquid nitrogen and then freeze-dried to yield the calcium salt of 5-phenyl-thiobarbituric acid as characterized by infrared spectroscopy.

B. Other Materials

1. Glycerol-1,3-dimethacrylate Phosphate

Reaction of 72 g glycerol-1,3-dimethacrylate with 17 g phosphorous pentoxide was performed under stirring, cooling with an ice bath and nitrogen atmosphere at room temperature for 48 hours to yield glycerol-1,3-dimethacrylate phosphate as a pale yellow liquid. The product was characterized by $^1$H- and $^{31}$P-NMR spectroscopy.

2. Propoxylated Bisphenol A Dimethacrylate

Reaction of 100 g Bisphenol A, 83 g 3-chloro-1-propanol and 49 g potassium hydroxide was performed at 100° C. in 300 ml ethylene glycol. After a reaction time of 10 hours, the reaction mixture was cooled to room temperature and water (300 ml) was added. Then the reaction mixture was extracted with 900 ml toluene. The combined toluene extracts were washed with 200 ml water. The solvent was evaporated under vacuum and an oily intermediate product was obtained.

The intermediate product was then dissolved in 400 ml benzene. 78 g methacrylic acid and 2 g sulfuric acid were added and the mixture was reacted for 12 hours under reflux using a water-cooled condenser. The reaction mixture was cooled to room temperature, extracted with 300 ml aqueous sodium hydroxide and additionally washed with 500 ml water. Finally the organic solvent was evaporated under vacuum and the final product was obtained as a pale yellow liquid. The product was characterized by $^1$H-NMR spectroscopy.

3. Triethylenglycol Dimethacrylate (Abbreviated as TEGDMA)

Commercially available from Roehm GmbH & Co. KG, Darmstadt, Germany.

4. Strontium Aluminium Fluorosilicate Glass (3% silane)

Non-reactive SR-GLASS (commercially available as GM 32087, particle size<12 μm from Schott Glaswerke, Landshut, Germany) was treated with 3% by weight methacryloxypropyltrimethoxysilane.

Example 1

A mixture of non-acidic methacrylates consisting of 5 g triethylenglycol dimethacrylate (TEGDMA) and 5 g propoxylated Bisphenol A dimethacrylate was prepared. 2.6 weight % of the calcium salt of 1-benzyl-5-phenyl-barbituric acid (abbreviated as Ca-BzPB) (prepared as described under MATERIALS) was added to the mixture and then stored at 23° C. and ambient humidity in closed container.

The mixture of monomers and salt was visually observed for polymerization. The monomer mixture did not polymerize in the presence of the salt over the time period observed. Results are summarized in Table 1.

Examples 2-4

Example 1 was repeated employing three other salts described above, respectively: sodium salt of 1-benzyl-5-phenyl-barbituric acid (abbreviated as Na-BzPB), triethanol ammonium salt of 1-benzyl-5-phenyl-barbituric acid (abbreviated as TEA-BzPB) and the calcium salt of 5-phenyl-thiobarbituric acid (abbreviated as Ca-PTB). None of these salts caused polymerization of the non-acidic methacrylate monomers when the mixtures were stored under ambient conditions. Results are summarized in Table 1.

Comparative Example 1

1-Benzyl-5-phenyl-barbituric acid (abbreviated as BzPBa) (2.6 wt %) was added to the monomer mixture described in Example 1-4. Polymerization was observed within 24 hours. The polymerization time was determined as described in the Test Method section above. Results are summarized in Table 1.

Comparative Example 2

5-Phenyl-thiobarbituric acid (abbreviated as PTBa) (2.6 wt %) was also added to the mixture of non-acidic methacrylate monomers described above. Polymerization occurred within 4 hours.

Examples 5-8

Acetic acid (0.33 g) was added to each of the mixtures described in Examples 1-4, respectively. The time required for polymerization was measured as described under Test Methods above and recorded. Results are summarized in Table 1.

Examples 9-12 p-Toluene sulfonic acid (0.27 g) was added to each of the mixtures described in Examples 1-4, respectively. The time required for polymerization was measured as described under Test Methods above and recorded. Results are summarized in Table 1.

Examples 13-16

Glycerol-1,3-dimethacrylate phosphate (2.5 g) was added to each of the mixtures described in Examples 1-4, respectively. The time required for polymerization was measured as described under Test Methods above and recorded. Results are summarized in Table 1.

Mixing of 1 part by weight of liquid A with 1 part by weight of liquid B resulted in a composition that polymerized after 20 minutes at 23° C.

Composition of the two components of Example 17 is summarized in Table 2.

TABLE 2

| Component | Weight % |
|---|---|
| Liquid A | |
| Propoxylated Bisphenol A dimethacrylate | 95.0 |
| Ca-BzPB | 5.0 |
| Liquid B | |
| Triethylenglycol dimethacrylate (TEGDMA) | 95.45 |

TABLE 1

| | | | Barbituric acid derivative | | | |
|---|---|---|---|---|---|---|
| Ex. | Monomer 1 | Monomer 2 | Free form | Salt form | Added acidic component | Polymer. time |
| 1 | X | X | — | Ca-BzPB | — | >1 mo |
| 2 | X | X | — | Na-BzPB | — | >1 mo |
| 3 | X | X | — | TEA-BzPB | — | >1 mo |
| 4 | X | X | — | Ca-PTB | — | >1 mo |
| C1 | X | X | BzPBa | — | — | 24 hrs |
| C2 | X | X | PTBa | — | — | 4 hrs |
| 5 | X | X | — | Ca-BzPB | Acetic acid | 3 hrs |
| 6 | X | X | — | Na-BzPB | Acetic acid | 3.25 hrs |
| 7 | X | X | — | TEA-BzPB | Acetic acid | 24 hrs |
| 8 | X | X | — | Ca-PTB | Acetic acid | 6 hrs |
| 9 | X | X | — | Ca-BzPB | p-Tol. sulfonic acid | 0.25 hrs |
| 10 | X | X | — | Na-BzPB | p-Tol. sulfonic acid | 0.3 hrs |
| 11 | X | X | — | TEA-BzPB | p-Tol. sulfonic acid | 2.0 hrs |
| 12 | X | X | — | Ca-PTB | p-Tol. sulfonic acid | 0.25 hrs |
| 13 | X | X | — | Ca-BzPB | Glycerol-1,3-dimethacrylate phosphate | 0.5 hrs |
| 14 | X | X | — | Na-BzPB | Glycerol-1,3-dimethacrylate phosphate | 1 hrs |
| 15 | X | X | — | TEA-BzPB | Glycerol-1,3-dimethacrylate phosphate | 5 hrs |
| 16 | X | X | — | Ca-PTB | Glycerol-1,3-dimethacrylate phosphate | 1.5 hrs |

Monomer 1 Triethylenglycol dimethacrylate
Monomer 2 Propoxylated Bisphenol A dimethacrylate
— None. Component not present.

Example 17

A first liquid component was prepared by combining 95 wt % propoxylated Bisphenol A dimethacrylate and 5 wt % calcium salt of 1-benzyl-5-phenyl-barbituric acid (Ca-BzPB).
A second liquid component was prepared by combining 95.45 wt. % triethylenglycol dimethacrylate (TEGDMA), 0.16 wt % Cu(II)-acetate accelerator and 4.39 wt % acetic acid.

TABLE 2-continued

| Component | Weight % |
|---|---|
| Cu(II)-acetate | 0.16 |
| Acetic acid | 4.39 |

Ca-BzPB: calcium salt of 1-benzyl-5-phenyl-barbituric acid

Example 18

Example 17 was repeated with two exceptions: the acid employed in the liquid B was 6.04 wt % glycerol-1,3-dimethacrylate phosphate (instead of acetic acid) and TEGDMA was reduced to 93.8 wt %.

Mixing of 1 part by weight of liquid A and 1 part by weight of liquid B resulted in a composition that polymerized after 18 minutes at 23° C.

Example 19

In Example 19, two paste components, each component comprising a filler, were prepared.

Paste A comprised two non-acidic methacrylate monomers, the calcium salt of 1-benzyl-5-phenyl-barbituric acid and 67 wt % of an acid-reactive FAS glass such as the commercially available G018-090 from Schott Glaswerke, Landshut, Germany.

Paste B comprised an acidic component (glycerol-1,3-dimethacrylate phosphate) an accelerator (copper acetate) and 70 wt % strontium aluminium fluorosilicate glass with 3% silane. Paste A and paste B were prepared by mixing the amounts of components given in the table below and then kneading the components together using commercially available kneading equipment.

Composition of the two components of Example 19 is summarized in Table 3.

TABLE 3

| Component | Weight % |
|---|---|
| Paste A | |
| Propoxylated Bisphenol A dimethacrylate | 15.0 |
| TEGDMA | 15.0 |
| Ca-BzPB | 3.0 |
| FAS glass (acid-reactive) | 67.0 |
| Paste B | |
| Glycerol-1,3-dimethacrylate phosphate | 29.9 |
| Cu(II)-acetate | 0.1 |
| Strontium aluminium fluorosilicate glass (non-reactive, 3% silane) | 70.0 |

TEGDMA: triethyleneglycol dimethacrylate

One (1) part by weight of paste A and 1 part by weight of paste B were then combined by hand mixing using a spatula and a mixing pad. The mixed paste started to set after about 8 minutes at 28° C.

What is claimed is:

1. A kit comprising:
   a first paste comprising a free-radically polymerizable composition comprising:
   (A) a compound having formula (I)

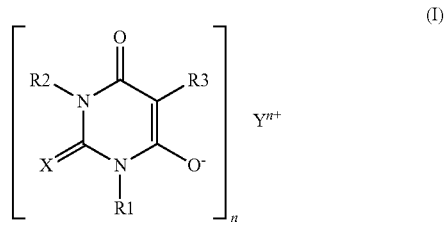

wherein R1, R2, and R3 are independently selected from hydrogen, alkyl, substituted alkyl, alkenyl, cycloalkyl, substituted cycloalkyl, arylalkyl, aryl or substituted aryl;
   X is oxygen or sulfur;
   Y is a metal cation having a +2 charge and
   (B) an ethylenically unsaturated compound without acid functionality; a second paste comprising:
   (C) an acidic component or precursor to an acidic component; and a means for mixing.

2. The kit of claim 1 wherein the first paste and the second paste form a stable mixture when mixed together.

3. The kit of claim 1, wherein the metal cation is a cation of Mg, Ca, Sr, Ba, Fe, Cu, or Zn.

4. The kit of claim 1, wherein the compound of formula (I) comprises the calcium salt of 1-benzyl-5-phenyl-barbituric acid.

5. The kit of claim 1, wherein the compound of formula (I) comprises the calcium salt of 5-phenyl-thiobarbituric acid.

6. The kit of claim 1, wherein the compound of formula (I) comprises the calcium salt of 1-benzyl-5-phenyl-barbituric acid, or the calcium salt of 5-phenyl-thiobarbituric acid.

7. The kit of claim 1, wherein the compound of formula (I) comprises the calcium salt of 1-benzyl-5-phenyl-barbituric acid, or the calcium salt of 5-phenyl-thiobarbituric acid, and the ethylenically unsaturated compound without acid functionality comprises a mixture of triethyleneglycol dimethacrylate and propoxylated Bisphenol A dimethacrylate.

8. The kit of claim 1, wherein the acidic component or precursor of acidic component is an ethylenically unsaturated compound.

9. The kit of claim 8, wherein the ethylenically unsaturated compound is 1,3-glycerol dimethacrylate phosphate.

10. The kit of claim 1, wherein the ethylenically unsaturated compound without acid functionality comprises an acrylate or a methacrylate.

11. The kit of claim 10, wherein the methacrylate is triethyleneglycol dimethacrylate, propoxylated Bisphenol A dimethacrylate, or a mixture of triethyleneglycol dimethacrylate and propoxylated Bisphenol A dimethacrylate.

12. The kit of claim 1, wherein the first paste further comprises an additive selected from the group consisting of a water adsorbent, a fumed silica, an accelerator, a pigment, a photoinitiator system, a redox cure system and a stabilizer.

13. The kit of claim 1, wherein the first paste further comprises a filler.

14. The kit of claim 1, wherein the second paste further comprises a compound having the formula $CuX_n$, wherein X is an organic or inorganic anion and n equals 1 or 2.

15. The kit of claim 1, wherein the acidic component or precursor of an acidic component has a pKa lower than that of the barbituric acid, thiobarbituric acid, barbituric acid derivative, or thiobarbituric acid derivative used for the synthesis of the compound of formula (I).

16. A method for curing a dental formulation comprising:
preparing a first paste, the first paste comprising
(A) a compound of formula (I)

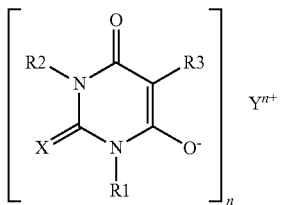

wherein R1, R2, and R3 are independently selected from hydrogen, alkyl, substituted alkyl, alkenyl, cycloalkyl, substituted cycloalkyl, arylalkyl, aryl or substituted aryl;

X is oxygen or sulfur;

Y is a metal cation having a +2 charge; and (B) an ethylenically unsaturated compound without acid functionality;

preparing a second paste, the second paste comprising (C) an acidic component, or a precursor of an acidic component and mixing together the first paste and the second paste.

17. The method of claim 16, wherein the amount of the acidic component or acid precursor component is such that mixing converts some of the compound of formula (I) into a form that is not a salt.

18. The method of claim 16, wherein the second paste further comprises a compound having the formula $CuX_n$, wherein X is an organic or inorganic anion and n equals 1 or 2.

19. The method of claim 16, wherein the acidic component or precursor of an acidic component has a pKa lower than that of the barbituric acid, thiobarbituric acid, barbituric acid derivative, or thiobarbituric acid derivative used for the synthesis of the compound of formula (I).

20. The method of claim 16, wherein a composition obtained by mixing the first paste with the second paste can cure in the absence of light.

21. A composition obtained by the method of claim 17.

* * * * *

UNITED STATES PATENT AND TRADEMARK OFFICE
CERTIFICATE OF CORRECTION

PATENT NO.         : 8,236,871 B2
APPLICATION NO.    : 12/302591
DATED              : August 7, 2012
INVENTOR(S)        : Reinhold Hecht It is certified that error appears in the above-identified patent and that said Letters Patent is hereby corrected as shown below:

On the Title Page, item [56], Col. 2 (U.S. Patent Documents):
Line 22              Delete "Bissigner" and insert -- Bissinger --, therefor.

In the Specification:

Column 4
Line 43              Delete "cyclo-alkyl" and insert -- cycloalkyl --, therefor.

Column 5
Line 3               Delete "tert.-butylamine," and insert -- tert-butylamine, --, therefor.
Line 10              Delete "di-tert.-butylamine," and insert -- di-tert-butylamine, --, therefor.
Line 16              Delete "tri-tert.-butylamine," and insert -- tri-tert-butylamine, --, therefor.
Lines 18-21          Delete "Dimethylethanolamine, N,N-dimethylaminoethylmethacrylate, triallylamine, tricyclopentylamine, tricyclohexylamine, tribenzylamine, triphenylethylamine, tripheny-lamine, trinaphthylamine." and insert -- dimethylethanolamine, N,N-dimethylaminoethylmethacrylate, triallylamine, tricyclopentylamine, tricyclohexylamine, tribenzylamine, triphenylethylamine, tripheny-lamine, trinaphthylamine. -- on Col. 5, Line 17 after "triethanolamine," as a continuation of the same paragraph.
Line 32              Delete "diphenylmethandiamine," and insert -- diphenylmethanediamine, --, therefor.
Line 33              Delete "Jeffamin," and insert -- Jeffamine, --, therefor.

Column 6
Lines 7-8            Delete "hexacrylate," and insert -- hexaacrylate, --, therefor.
Line 11              Delete "bisphenolA" and insert -- bisphenol A --, therefor.
Line 39              Delete "(meth)-acrylate;" and insert -- (meth)acrylate; --, therefor.

Signed and Sealed this
Eighteenth Day of June, 2013

Teresa Stanek Rea
*Acting Director of the United States Patent and Trademark Office*

CERTIFICATE OF CORRECTION (continued)
U.S. Pat. No. 8,236,871 B2

In the Specification (Cont'd):

Column 8
Line 16                      Delete "acide" and insert -- acid --, therefor.

Column 9
Line 17                      Delete "photo-polymerizable" and insert -- photopolymerizable --, therefor.
Line 18                      After "described" insert -- in --.
Line 39                      Delete "hexacrylate," and insert -- hexaacrylate, --, therefor.
Line 41                      Delete "propoxy-phenyldimethylmethane," and insert
                                    -- propoxyphenyldimethylmethane, --, therefor.
Line 42                      Delete "bisphenolA" and insert -- bisphenol A --, therefor.

Column 10
Line 3                        Delete "(meth)-acrylate;" and insert -- (meth)acrylate; --, therefor.
Line 18                      Delete "desired)." and insert -- desired. --, therefor.
Line 27                      Delete "diphenyl-iodonium" and insert -- diphenyliodonium --, therefor.
Lines 35-36                Delete "tetramethylcyclo-hexanedione," and insert
                                    -- tetramethylcyclohexanedione, --, therefor.

Column 11
Line 16                      Delete "unimodial" and insert -- unimodal --, therefor.
Line 16                      Delete "polymodial" and insert -- polymodal --, therefor.

Column 12
Lines 18-19                Delete "mercaptopropyltriethoxy-silane," and insert
                                    -- mercaptopropyltriethoxysilane, --, therefor.

Column 13
Line 34                      Delete "intiator" and insert -- initiator --, therefor.
Line 60                      Delete "$C_4$ to $C_7$" and insert -- C4 to C7 --, therefor.

Column 16
Line 11 (Approx.)       Delete "Triethylenglycol" and insert -- Triethyleneglycol --, therefor.
Lines 19-20                Delete "methacryloxypropyltrimethoxylsilane." and insert
                                    -- methacryloxypropyltrimethoxysilane. --, therefor.
Line 25                      Delete "triethylenglycol" and insert -- triethyleneglycol --, therefor.
Line 52                      Delete "Example" and insert -- Examples --, therefor.

Columns 17-18
Line 3 (Table 1)           Delete "Polymer." and insert -- Polymer --, therefor.

Column 17
Line 54 (Approx.)       Delete "Triethylenglycol" and insert -- Triethyleneglycol --, therefor.
Line 65                      Delete "triethylenglycol" and insert -- triethyleneglycol --, therefor.

CERTIFICATE OF CORRECTION (continued)
U.S. Pat. No. 8,236,871 B2

In the Specification (Cont'd):

Column 18
Line 17 (Approx.)   Delete "Triethylenglycol" and insert -- Triethyleneglycol --, therefor.